US010786649B2

(12) United States Patent
McLaughlin et al.

(10) Patent No.: US 10,786,649 B2
(45) Date of Patent: Sep. 29, 2020

(54) IMMERSIVE SYSTEM FOR RESTORATIVE HEALTH AND WELLNESS

(71) Applicant: SRI International, Menlo Park, CA (US)

(72) Inventors: Glen W. McLaughlin, San Carlos, CA (US); Massimiliano de Zambotti, Burlingame, CA (US); Fiona C. Baker, San Jose, CA (US); Ian M. Colrain, Redwood City, CA (US)

(73) Assignee: SRI International, Menlo Park, CA (US)

( * ) Notice: Subject to any disclaimer, the term of this patent is extended or adjusted under 35 U.S.C. 154(b) by 224 days.

(21) Appl. No.: 15/863,881

(22) Filed: Jan. 6, 2018

(65) Prior Publication Data

US 2018/0193589 A1    Jul. 12, 2018

Related U.S. Application Data

(60) Provisional application No. 62/443,336, filed on Jan. 6, 2017.

(51) Int. Cl.
*A61M 21/02* (2006.01)
*A61B 5/00* (2006.01)
(Continued)

(52) U.S. Cl.
CPC ......... *A61M 21/02* (2013.01); *A61B 5/02055* (2013.01); *A61B 5/486* (2013.01);
(Continued)

(58) Field of Classification Search
CPC .............. A61M 21/02; A61M 2230/65; A61M 2230/63; A61M 2230/50; A61M 2230/42;
(Continued)

(56) References Cited

U.S. PATENT DOCUMENTS

| 9,872,968 B2 | 1/2018 | deZambotti et al. | |
| 2002/0171551 A1* | 11/2002 | Eshelman | G06Q 50/22 340/573.1 |
| 2014/0316191 A1* | 10/2014 | de Zambotti | A61M 21/02 600/27 |

OTHER PUBLICATIONS

Rick Downs. "Understanding the Tradeoff of Increasing Resolution by Averaging". Jan. 11, 2012. Electronic Design. https://www.electronicdesign.com/analog/understand-tradeoffs-increasing-resolution-averaging (Year: 2012).*

* cited by examiner

*Primary Examiner* — Christine H Matthews
*Assistant Examiner* — Joshua Daryl D Lannu
(74) *Attorney, Agent, or Firm* — Moser Taboada

(57) ABSTRACT

A restorative health and wellness system that provides an immersive environment is provided herein. In some embodiments, the system includes one or more sensors configured to measure physiological properties of an individual and/or the properties of the individual's surroundings, one or more actuators configured to create the immersive environment for the individual, a control loop module configured to receive and analyze input from the one or more sensors, and to provide information to the actuators to create the immersive environment for the individual, wherein the one or more actuators dynamically create or adjust the immersive environment based on at least one of (A) the physiological properties measured or (B) the properties of the individual's surroundings, and at least one of (A) a pre-determined individual priority balance set for the individual or (B) an optimized set of parameters determined through advanced analytic techniques.

25 Claims, 8 Drawing Sheets

(51) Int. Cl.
*G06F 3/01* (2006.01)
*A61B 5/0205* (2006.01)
*G16H 20/70* (2018.01)
*G16H 50/30* (2018.01)
*A61M 21/00* (2006.01)
*A61B 5/0488* (2006.01)
*A61B 5/0476* (2006.01)
*A61B 5/0402* (2006.01)
*A61B 5/053* (2006.01)
*A61B 5/11* (2006.01)
*G16H 40/63* (2018.01)

(52) U.S. Cl.
CPC ............ *A61B 5/4815* (2013.01); *G06F 3/011* (2013.01); *G06F 3/015* (2013.01); *G06F 3/016* (2013.01); *G16H 20/70* (2018.01); *G16H 50/30* (2018.01); *A61B 5/0006* (2013.01); *A61B 5/0402* (2013.01); *A61B 5/0476* (2013.01); *A61B 5/0488* (2013.01); *A61B 5/053* (2013.01); *A61B 5/11* (2013.01); *A61M 2021/005* (2013.01); *A61M 2021/0022* (2013.01); *A61M 2021/0027* (2013.01); *A61M 2021/0044* (2013.01); *A61M 2021/0066* (2013.01); *A61M 2021/0072* (2013.01); *A61M 2205/3375* (2013.01); *A61M 2205/3553* (2013.01); *A61M 2205/3592* (2013.01); *A61M 2205/507* (2013.01); *A61M 2230/06* (2013.01); *A61M 2230/10* (2013.01); *A61M 2230/30* (2013.01); *A61M 2230/42* (2013.01); *A61M 2230/50* (2013.01); *A61M 2230/63* (2013.01); *A61M 2230/65* (2013.01); *G06F 2203/011* (2013.01); *G16H 40/63* (2018.01)

(58) Field of Classification Search
CPC .......... A61M 2230/30; A61M 2230/10; A61M 2230/06; A61M 2205/507; A61M 2205/3592; A61M 2205/3553; A61M 2205/3375; A61M 2021/0072; A61M 2021/0066; A61M 2021/0044; A61M 2021/0027; A61M 2021/0022; A61M 2021/005; A61M 2230/005; A61B 5/486; A61B 5/0006; A61B 5/02055; A61B 5/0402; A61B 5/0476; A61B 5/0488; A61B 5/053; A61B 5/11; A61B 5/4815; G06F 3/015; G06F 3/011; G06F 3/016; G06F 2203/011; G16H 20/70; G16H 40/63; G16H 50/30
See application file for complete search history.

US 10,786,649 B2

IMMERSIVE SYSTEM FOR RESTORATIVE HEALTH AND WELLNESS

CROSS-REFERENCE

This application claims benefit of U.S. provisional patent application Ser. No. 62/443,336, filed Jan. 6, 2017. The aforementioned provisional patent application is herein incorporated by reference in its entirety.

FIELD

This disclosure relates generally to devices, methods, and systems for providing an immersive user experience within an immersive environment system, and more specifically to an immersive environment platform for restorative health and wellness applications.

BACKGROUND

Many people struggle with physical and mental health disorders. These physical and mental health issues include sleep disorders, vices (smoking, gambling, etc.), post-traumatic stress disorder, phobia/anxiety, blood pressure, chronic pain, exhaustion, mediation, prejudices, headaches, weight control as well as a number of others. These disorders can also be divided into clinical and non-clinical. The Diagnostic and Statistical Manual of Mental Disorders, Fifth Edition, (DSM-5) is the currently acceptance way to classify the clinical disorders while the non-clinical do not yet have a well-accepted classification method to assist in the understanding of the principle components that need to be addressed.

Cognitive-Behavioral Therapy (CBT) and pharmacotherapy are two main lines of treatment that are currently available to treat these types of disorders. However, however, many people who suffer from the above afflictions do not wish to use pharmacotherapy and there is limited availability of CBT.

Thus, there is a need for improved systems and methods centered on enabling each individual user to re-gain balance from either episodic environmental disturbances or chronic disturbances.

SUMMARY

A restorative health and wellness system that provides an immersive environment is provided herein. In some embodiments, a restorative health and wellness system that provides an immersive environment includes one or more sensors configured to measure physiological properties of an individual and/or the properties of the individual's surroundings, one or more actuators configured to create the immersive environment for the individual, wherein the immersive environment is an environment that attempts to improve sleep quality or relaxation by immersing the individual in an optimal environment, a control loop module configured to receive and analyze input from the one or more sensors, and to provide information to the actuators to create the immersive environment for the individual, and one or more communications devices configured to facilitate communications between the one or more sensors, the one or more actuators, and the individual, wherein the one or more actuators dynamically create or adjust the immersive environment based on at least one of (A) the physiological properties of the individual measured by the one or more sensors or (B) the properties of the individual's surroundings measured by the one or more sensors, and at least one of (A) a pre-determined individual priority balance set for the individual or (B) an optimized set of parameters determined through advanced analytic techniques.

In some embodiments, a restorative health and wellness system that provides an immersive audio environment includes one or more sensors configured to measure physiological properties of an individual and/or audio signals from an individual's environment, one or more audio actuators configured to create the immersive audio environment for the individual, wherein the immersive audio environment is an environment that attempts to improve sleep quality or relaxation by immersing the individual in an optimal audio environment, a control loop module configured to receive and analyze input from the one or more sensors, and to provide information to the audio actuators to create the immersive audio environment for the individual, and one or more communications devices configured to facilitate communications between the one or more sensors, the one or more audio actuators, and the individual, wherein the one or more audio actuators dynamically create or adjust the immersive audio environment based on at least one of (A) the physiological properties of the individual measured by the one or more sensors or (B) the audio signals from an individual's environment measured by the one or more sensors, and at least one of (A) a pre-determined individual priority balance set for the individual or (B) an optimized set of audio parameters determined through advanced analytic techniques.

In some embodiments, computer implemented method for a restorative health and wellness system that provides an immersive environment includes receiving, from one or more audio sensors, audio signals from an individual's environment, receiving, from one or more physiological sensors, physiological properties measured from of an individual, receiving and processing the physiological properties and audio signals using a control loop module, determining, by the control loop module, whether the audio signals received are affecting the individual's physiological state, and when it is determined that the audio signals received are negatively affecting the individual's physiological state, then instructing one or more actuators to at least one of modify, decrease, cancel, drown out, or filter the audio signals received, wherein the one or more actuators dynamically create or adjust the immersive environment based on at least one of (A) the physiological properties of the individual measured by the one or more sensors or (B) the properties of the individual's surroundings measured by the one or more sensors, and at least one of (A) a pre-determined individual priority balance set for the individual or (B) an optimized set of parameters determined through advanced analytic techniques.

Other and further embodiments of the present disclosure are described below.

DRAWINGS

This disclosure is illustrated by way of example and not by way of limitation in the accompanying figures. The figures may, alone or in combination, illustrate one or more embodiments of the disclosure. Elements illustrated in the figures are not necessarily drawn to scale. Reference labels may be repeated among the figures to indicate corresponding or analogous elements.

DESCRIPTION

Figure 1:
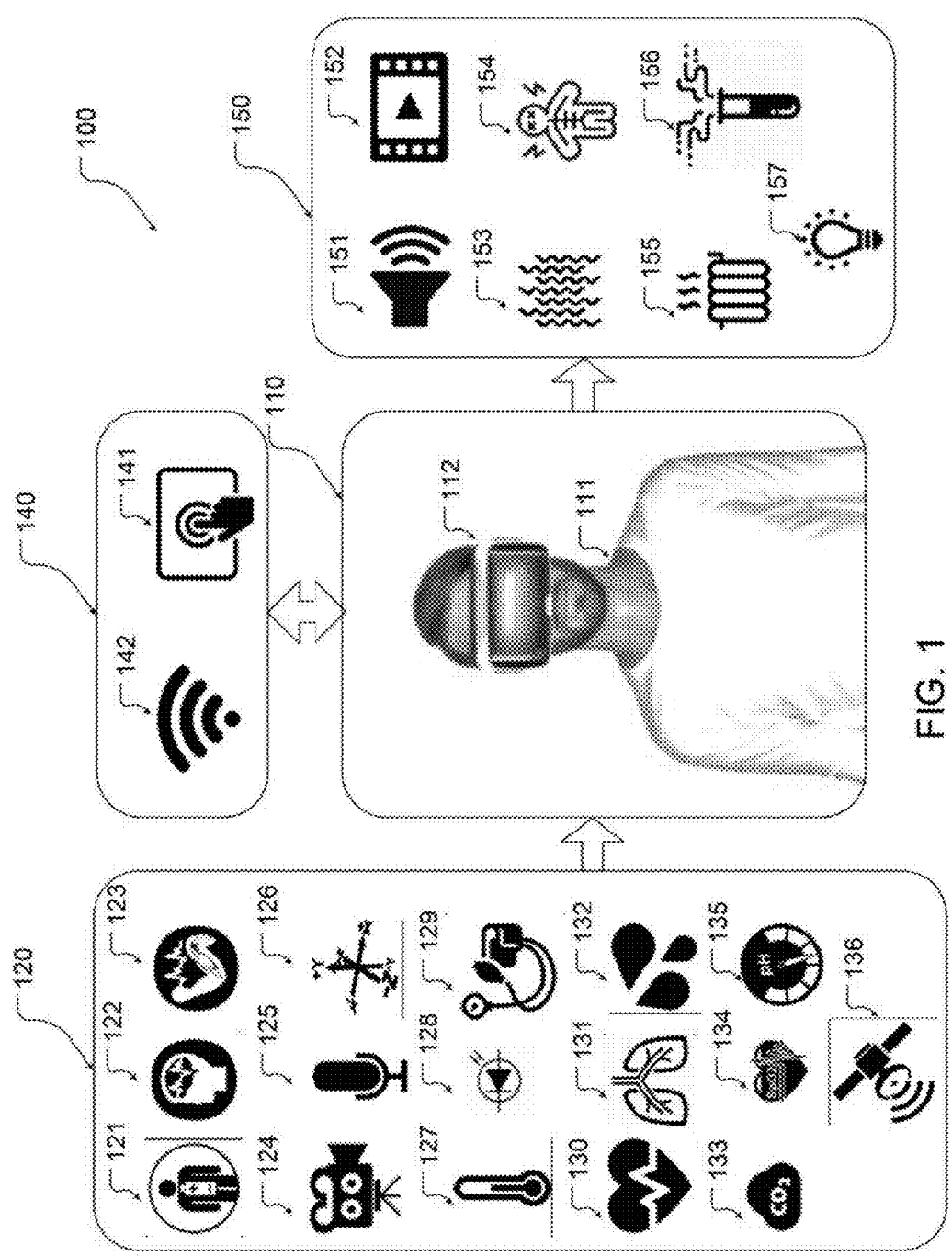
FIG. 1 is a simplified schematic diagram of an embodiment of a system architecture for an immersive system for the use of restorative health and wellness applications, including sensor based inputs, communications based devices and actuator based outputs.

This disclosure describes inventive concepts and technologies with reference to specific examples. However, the intent is to cover all modifications, equivalents, and alternatives of the inventive concepts and technologies that are consistent with this disclosure.

Many people struggle with their physical and mental health (e.g., back pain, insomnia, mood, etc.). This disclosure describes a platform, system, and methods for providing an immersive system that modulates established physiologic control paths through the use of electronic, electromechanical, mechanical, or other types of actuator devices ('actuators'), and measures changes in the user's physiological state through the use of one or more sensing devices ('sensors'). The platform, system, and methods described in this document are implemented using one or more computing devices that may form or be part of a networked system in which the computing devices communicate with each other through e.g. wired or wireless electronic or optical communication paths. The actuators may be controlled based on output of one or more fixed machine-learning algorithms and/or adaptive machine-learning algorithms, which may be configured or trained based on data obtained from cognitive behavioral science studies. The changes in physiological measurements can be fed back to the machine learning algorithm(s) to provide a closed loop control system for the immersive environment that is generated by the system.

Some versions of the system may utilize an immersive environment system equipped with sensors and actuators that can be built into a headset or placed on or around the user's body. In versions of the disclosed system, a restorative health and wellness system is designed for a comfortable and natural feel whether it is in the form of a headset or an adaptive immersive environment surrounding the user. In order to achieve restorative health and/or wellness objectives, the immersive system is configured to draw the user into an optimal immersive virtual reality environment to the point that over time the user forgets that they are actually wearing a headset at all, or surrounded by the equipment creating the immersive environment. In some embodiments, the optimal environment in which the individual is immersed in is one that induces maximum relaxation and/or generates a higher sleep quality score, as described below. In this way, individuals may improve their mental and/or physical condition without requiring a medical solution. In some embodiments, the headset is a symbolic representation of one or more displays, acoustic speakers, and other actuators that create the immersive environment for the user.

In one embodiment, immersion into virtual reality is a perception of being physically present in a non-physical world. The perception is created by surrounding the user of the immersive environment system in sound or other stimuli that provide an engrossing total environment. As a clarification, virtual reality is one form of immersive reality, but immersive reality is not limited to the virtual reality. Typically, virtual reality focuses on the visual environment. However, in at least some embodiments consistent with the present invention, an immersive environment is described that focuses on sound/audio signals. The degree to which the immersive environment faithfully reproduces reality determines the degree of suspension of disbelief. The greater the suspension of disbelief, the greater the degree of presence achieved. Presence is a phenomenon enabling people to interact with and feel connected to the world outside their physical bodies via technology. It is defined as a person's subjective sensation of being there in a scene depicted by a medium, usually virtual in nature. It is the individual's subjective perception, although generated by and/or filtered through human-made technology that ultimately determines the successful attainment of presence.

An immersive digital environment is an artificial, interactive, computer-created scene or "world" within which a user can immerse themselves. Immersive digital environments could be thought of as synonymous with virtual reality, but without the implication that actual "reality" is being simulated. An immersive digital environment could be a model of reality, but it could also be a complete fantasy user interface or abstraction, as long as the user of the environment is immersed within it. The definition of immersion is wide and variable, but here it is assumed to mean simply that the user feels like they are part of the simulated "universe". The success with which an immersive digital environment can actually immerse the user is dependent on many factors such as believable 3D computer graphics, surround sound, interactive user-input and other factors such as simplicity, functionality and potential for enjoyment. New technologies are currently under development that claim to bring realistic environmental effects to the players' environment—effects like wind, seat vibration and ambient lighting.

Restorative health and wellness is a generalized field that has been addressed, in the past, both from a scientific as well as a spiritual standpoint. Results have been inconsistent due to internal changes within an individual's physiologic set points or the individual's lack of compliance with the therapy or wellness protocol over time. One example of a scientific approach that ultimately fails over the long-term is the use of pharmaceuticals to treat chronic pain. As an individual builds up a tolerance for the medication (e.g. pain killers), the individual needs to continue to keep taking larger and larger doses. This may continue until the individual ultimately takes a lethal amount of the painkiller, or returns to suffering from the original pain. However, as a result of having completed the medication regimen, at this point the individual's internal physiologic pain set point (tolerance to pain) may have been modified such that the original pain level is amplified.

Weight control is a well-documented restorative health and wellness application that suffers from long-term compliance issues. The diet industry promotes short term results through caloric restriction but instead of achieving the desired long term weight loss, the body adjusts its basal metabolic level to be in equilibrium with the current caloric intake so that when the individual returns to normal eating habits not only do they regain their weight quickly but typically overshoot to an even higher weight.

In contrast to prior restorative health and wellness approaches, this system describes an approach that can improve on a number of the existing techniques by providing an environment that has the ability to retain its novelty (and thus, the interest of the user) over an extended period of time by adapting the user experience to the changes in the user's physiologic states over time. The disclosed approach can interact with established physiologic pathways to create a closed loop control system with the use of sensors and actuators that actively measure and modulate these physiologic pathways, in order to produce sustained results along with a high level of compliance through positive reinforcement.

A system is described that integrates immersive environment/virtual reality technologies with advanced physiologic sensors and actuators, thereby enabling immersive environment system to operate in a closed loop control manner designed to encourage long lasting physiologic and psychological behavioral modifications to its users. As used in this document, "closed loop" may refer to, e.g., feedback and/or feed-forward control systems and methods.

The disclosed restorative health and wellness technologies focus on measuring, modulating and adapting the modulation stimulus of physiological pathways to assist in restoring appropriate set points to regain internal homeostasis. The measurements used to obtain homeostasis are obtained from the user, the user's external physical environment, and/or the user's interactions with his or her environment. These measurements are used to guide the user's behavior to improve his or her health.

Some aspects of the disclosed technologies are designed to enable each individual user to re-gain balance from episodic environmental disturbances or chronic disturbances. Some illustrative areas of focus where these technologies can assist are as follows: sleep, vices (smoking, gambling, etc.), post-traumatic stress disorder, phobias, anxiety, blood pressure, chronic pain, exhaustion, mediation, prejudices, headaches, weight control as well as a number of others including relaxation. These disorders can also be divided into clinical and non-clinical. The Diagnostic and Statistical Manual of Mental Disorders, Fifth Edition (DSM-5) is a currently accepted reference for classifying clinical disorders. Non-clinical disorders do not yet have a well-accepted classification method to assist in the understanding of the principle components that need to be addressed and thus may be referred to simply as "non-clinical."

This disclosure further describes a system designed to track and adapt to changes in an individual's physiologic and/or psychological patterns based on both internal and external stressors for improving the individual's overall well-being.

The technologies described in this disclosure can create a computer-generated immersive environment that is presented to the user by an electronic device such as headphones, ear buds, surround sound speakers, a virtual reality headset, smart speakers and television equipment, projection system, mobile devices, smart glasses, or other suitable apparatus. Techniques and approaches described in United States Patent Application Publication No. US 20140316191 may be utilized in some embodiments, the contents of which are herein incorporated by reference in its entirety.

The illustrative immersive environment headset is designed to interface with the user's face via a face-headset interface. The face-headset interface may advantageously be made of a conforming material that has properties similar to that of the surrounding environment; for example, the thermal properties of the headset may be adjusted so that the headset neither pulls heat nor prevents the flow of heat away from the user's face in a manner that is any different from that of the surrounding air. The headset is designed so that when the headset is worn by the user, the face-headset interface portion of the headset and the user's face define an enclosed cavity (i.e. the space between the user's face and the interior surface of the headset and viewing screen). This face-headset interface portion of the headset device may be constructed with a material that is configured to maintain a neutral temperature gradient to the outside environment. The face-headset interface can be configured to adhere to the user's head or face in a manner that does not result in long-term irritations or fatigue to the user. For instance, a mechanical mechanism (e.g., a fastener) may affix the headset to the face in a conformal manner. Some versions of the headset may provide audio output. The headset may further include video capabilities that can function as a visual actuator in addition to providing physiological data that may be used for control loop modulation.

The headset may contain a battery that is able to power the unit so the headset can operate when not tethered to an external power source. Some versions of the headset are configured to be self-contained in operation. Some versions of the headset may be connectable to external sensors and actuators that may be used in the modulation of various closed loop control mechanisms, which may communicate with the headset via a wireless mechanism and a simple user interface. This wireless communication may include a low power communication channel, a direct connection, or a higher power communication channel. Some examples of wireless communication standards include but are not limited to are Bluetooth, ZigBee, 802.11, MICS, or similar protocols. The headset system may have an alternative mechanism of control, such as by an external computer or a smartphone.

The user interface may include a touch pad mounted on a front surface of the headset or a hand motion/gesture sensor that detects and interprets hand based commands by the user based on a sensor array disposed on the surface of the headset. The user interface may be used to configure and initiate a restorative health session of the system. In general, the immersive environment system architecture includes a central processing unit (CPU) that is capable of supporting either a single display channel or a dual display channel. The CPU may be configured to support audio capabilities and may store the immersive experience virtual world (e.g. audio, or graphics and video files) locally. The CPU is configured to render the immersive environment experience in a real time manner based on the control loop control and the user's interactions, or as a prerecorded immersive audio/video, or as a combination of interactive user experience and prerecorded content. Some versions of the headset can receive immersive environment content that is streamed directly to the device, in which case the immersive environment content need not be stored or processed locally on the device. Some versions of the headset device may store all of the sensor data and the control signals that are sent to the actuators. This data can be directly streamed to a data storage repository interfaced to the Internet or locally buffered until the device has an appropriate communication channel for transmitting the information to the data storage repository. In some versions of the system, the sensor/actuator/control parameter data set may be transferred to an intermediary device such as a smart phone or personal computer to be used to preprocess this information for parameter extraction, in order to reduce the need for long-term cloud storage requirements.

Examples of the types of sensors that can be used in or interfaced with the device to measure the physiologic properties of the individual as well as the physical environment that surrounds the user include: audio input, basal metabolic rate sensor, EEG sensor, EMG sensor, video input, multi access accelerometer, temperature sensor, light sensor, blood pressure sensor, general pressure sensor, EKG sensor, respiratory sensor, sweat sensor, CO2 sensor, SpO2 sensor, pH sensor, GPS, flow sensor and the like. Examples of the types of actuators the headset may contain or be connected with include: audio output, video output, vibration generator, electro shock generator, thermal generator, chemical essence generator, light generator of multiple colors and the like. A single sensor or actuator may be used to perform multiple different functions. For example, an electro shock generator may be used to both relax muscles to help reduce pain and also as a nerve stimulation to improve concentration or focus of the individual as well as increase sleep and relaxation. Depending on the restorative health and wellness application that the headset is configured to provide, the system can select the appropriate subset of the sensors and actuators to be used. For example, if an individual has headphones or a surround sound speaker system configured to assist them with sleeping, the primary set of sensors may be a method to measure heart rate variability and the main actuator may include an audio channel/speaker. Other sensors that can be used in this manner include the multi-axes accelerometer to measure position of the head to instruct the rendering engine what view needs to be displayed on the screen. Some versions of the headset may interface with a number of additional third party devices (such as mHealth devices) and other applications that may produce data usable as activity indicators (e.g., email, social media, SMS (short messaging service), GPS (global positioning system) location data and local news feeds). In some embodiments, the properties of the individual's surroundings can include signals from other individuals or animals that are close to the individual (e.g., a person's bedtime partner, a pet dog, etc.). For example, in some embodiments, a restorative health and wellness system that provides an immersive audio environment that can measure a noise (e.g., snoring) coming from a person's bedtime partner. The immersive environment system would dynamically create or adjust the individual's immersive audio environment based on the other person's snoring to modify, decrease, cancel, drown out, or filter the offending snoring noise in order to improve sleep quality or relaxation by immersing the individual in an optimal audio environment Some versions of the system are configurable so that the sensors contained within the headset are changeable/removable based on the application. To accomplish this, the exchangeable sensors may be located within or on a gasket of the headset that interfaces with the face of the user. In some versions, the gasket is removable and replaceable. The interface of the gasket to the headset may include an electronic as well as a mechanical attachment. In some versions, a small module may be provided alternatively or in addition to the gasket. The module can interface with other headsets that are controlled either by smart phones or by computers to transform those devices into a similar type of closed loop control headset.

When taking into account a more holistic manner of an individual's restorative health and wellness needs it is not only the individual and the time that therapy is being provided that needs to be considered, but also the surrounding environment along with indications of how the environment has modified the individual's well-being. These modifications occur both during the restorative health and wellness sessions as well as outside the sessions, so the ability to gather and use the information about the individual's interactions throughout their day provides an additional dimension in optimizing the system to better meet the user's needs. Some examples of stressors in the external environment are crowds of people, interaction with people, noise, animals, city stressors, pollution, and the like. Over time individuals tend to adapt to minimize their conscious reactions to these types of environmental stressors, but these stressors still continue to take a toll on an individual's wellbeing. Thus, being able to monitor and measure the continual assault of these types of stressors and utilize this information can greatly assist in the task of generating a custom tailored immersive environment based restorative health and wellness offering to meet the unique needs of the individual. This data can be stored for all users of the headset so that the collective learning of the set of headset users can be shared to ensure that each individual is receiving the best and most current set of optimized parameters.

The disclosed immersive environment system can measure and modulate known physiological control paths for providing restorative health and wellness sessions. In order to effectively accomplish this, the headset senses one or more stimulus signals with one or more sensors. The information generated from the sensor(s) can be used as an input to a control system. This control system can be static or adaptive. An advantage of an adaptive control system is that it can be optimized on an ongoing basis to a particular individual's needs. Versions of the adaptive control system may adapt within the same session and/or across different sessions. The inputs to the control system may include information obtained by the sensors and/or additional ancillary information from the individual or their family history like gender, age, weight, height, habits (eating, sleeping, drinking, smoking, etc.), known disease states, medications being used, family history of diseases and the like. This ancillary information can be used to segment or weight other users of the headset who have similar demographics in a higher category to those who are less correlated for the purpose of individualized therapy optimization.

The output of the control system modulates an actuator or actuators for optimizing the stimuli to obtain the desired restorative health and wellness result. For example, if the desired restorative health and wellness therapy were to assist in the promotion of sleep, there may be three possible types of control system: user biological signals, environmental, and psychosocial/social behavior, that can be used for overall optimum results.

For the user's biological signals, the stimulus may be to instruct the individual to perform deep abdominal breathing. The two possible sensors may be to either/or monitor the heart rate variability or the respiratory rate. The control loop can use the reading of heart rate variability and/or respiratory rate to estimate the current physiologic arousal level of the individual and based on the reading can modulate both the audio and video signals to drive the individual into a lower and lower level of arousal until sleep is induced. For example, once the user is in compliance with a slow respiratory rate the system can start a guided journey through a relaxing immersive world including graphics and sounds of, for example, a bamboo forest. As the user continued to keep their physiological settings in compliance the journey would continue if the user became distracted the journey might cease moving or might switch to a different immersive virtual world, for example, visual and audio simulating traveling through outer space. As the user traverses these virtual worlds, movements of their head may be tracked by the system, resulting in increasing the immersive experience as well as an audio background. There are also a number of additional items that may be used to assist, for example in the bamboo virtual world the bamboo can sway back and forth at a rate that is based on the user's respiratory rate or the rate of flow of water flowing over rocks in a brook may be synchronized with the user's heart rate to further enhance the connection between the user and the immersive environment. As the user becomes more relaxed, the overall intensity of the virtual world may decrease as if the sun were setting. The above are just a few examples of the many number of scenarios that can be used as primary as well as secondary closed loop control mechanisms with the disclosed system.

An example of an environmental control loop that can be employed to help promote sleep includes traffic noise as a stimulus. A sensor may be used to detect the traffic noise, e.g. an external microphone. The signals from the microphone can be transmitted into a control loop that is optimized to generate a signal that is used to cancel the traffic noise. This noise canceling signal is transmitted to an actuator or headphones to minimize the stimulus and prevent sleep disruption.

A psychosocial or social behavioral control loop may function outside the direct restorative health and wellness therapy session but may act as a conditioning element to ensure the user is in the proper reference frame when desired. An example of a potential stimulus that may be distracting to sleep is an individual who is responding to a number of incoming work related emails close in to the time that they typically go to sleep. The sensor can be an application running on the user's computer or phone that monitors outgoing email traffic from the user's work account. The control may include generating an SMS message or email to the user to "Take a break" once a certain threshold is reached. This control loop is configured to send the message to e.g. an SMS or email server for delivery to the user.

In order to enhance the overall experience of the immersive environment, advanced/predictive analytic techniques may be used on the data collected by the sensors (e.g., 120 in FIG. 1 described below), and/or the historical data collected with respect to the properties of the individual's surroundings. Such predictive analytics encompasses a variety of statistical techniques from predictive modelling, machine learning, and data mining that analyze current and historical facts to make predictions about future or otherwise unknown events. Other analytic techniques used to analyze/process the data to create an optimal immersive environment may also include rule-based models where the rules may be set based on the user's personal preferences or preferences of similarly situated individuals, if then logic, and the like. The output of all these advanced analytic techniques are an optimized set of parameters that are used to drive the actuators 150 of FIG. 1 to provide an optimal immersive environment for the individual. For example, the optimal set of parameters may include the selection, volume, frequencies of the sound, and amount of audio signals to provide to the user. The optimal set of parameters may include whether to modify, filter, cancel, or drown out various sounds negatively affecting a user. The optimal set of parameters may further include if, when and how to provide certain stimulus to the user in the form of audio output, video output, vibration generator, electro shock or electrical current generator, thermal generator, chemical essence generator, light generator of multiple colors and the like. Other examples of the parameters determined by advanced/predictive analytic techniques may include the combination of actuators used to create the immersive environment. Various examples of actuators and the types of outputs they provide are described herein. Each of those actuators described herein is controlled by the parameters provided to the actuators, which are determined through advanced analytic techniques.

In embodiments consistent with the present invention, one of the advanced analytic techniques can include machine learning. Machine learning techniques can be used to tailor overall performance of the headset to support the restorative health and wellness needs of each individual user. In the generation of the parameters for the machine learning algorithm the data used for the classification or regression can be built around the data gathered from all users and all the applications of restorative health and wellness to an intermediary level and then for final classification/regression a parametric fit can be generated for the specific application providing a further level of refinement. It is possible to extract information out of data collected from other restorative health and wellness applications not directly associated with a particular application to create an intermediary classifier through machine learning and as a second step use the application specific collected data for final classification/regression, as such the entire restorative health and wellness database at that moment of time of the users of the headset has the ability to be incorporated in the generation of an intermediate parametric set and then for the final stage of classification the targeted set of data can be used to obtain a higher quality classifier. As information is added to the database over time, this step can be repeated. An illustrative way to generate such an algorithm would be to obtain start with a family of guesses of reasonable parametric sets and use the data collected from the individual's sensor and actuator data to refine the guesses in either an online or an offline manner. As additional information is gathered the overall parameters can continually be modified, improving the match between the actual parameter set to that of the desired unknown target parameter set. The generation of this unknown optimum set of parameters can be accomplished by currently available methods. Some of the machine learning techniques that may be used but not limited to are as follows: decision tree learning, association rule learning, artificial neural networks, inductive logic, support vector, clustering, Bayesian networks, reinforcement learning, representation learning, similarity and metric learning, sparse dictionary learning, genetic algorithms, a weighted combination or voting based method of the above and the like. If it is preferred that the generation of the training based parameter set be done via an offline manner from the immersive environment system, then computational time or efficiency do not need to be completed in a real time manner. In some versions of the system, real time based optimization of the parameter set may be done directly within the immersive environment system to achieve even a tighter optimization of the control loop parameters for each individual user. In some embodiments, the optimized set of parameters determined through machine learning techniques is based on historical data collected with respect to the properties of the individual's surroundings. In some embodiments, the optimized set of parameters determined through machine learning techniques is based on the use of aggregated data of properties measured from other individuals retrieved from a cloud-computing environment or other external devices to train a machine learning model and provide a custom user-specific experience.

The immersive environment system may be configured in a similar manner to many commercially available complex communication devices intended for individual use; such as a laptop computer, smart phone, tablet device, headphones, ear buds, surround sound speakers, smart speakers and television equipment, but may have greater constraints on the packaging. For example, the packaging of an immersive environment system headset may be configured to retain a natural and comfortable user experience when worn for extended period of time. The basic system architecture of the headset includes a central processing unit (CPU). The structure of the CPU is more of a system on a chip (SOC) than a standard personal computer CPU. As such, this CPU ideally would have additional capabilities like a built in real time clock, video driver, audio drive, interface ports to external sensors/actuators, memory interface and the like. This high level of integration is desired not only from the savings of space and weight but also in power and system level complexity. The overall system may be powered via an internal battery. Li-Ion may be a preferred battery chemistry as it has a high power density relationship and can be constructed in a customized form-fitting configuration. Other battery chemistries that offer superior performance metrics may also be used. The battery may be configured as a smart battery and as such, the overall status of the remaining capacity, time to full charge, temperature, time to full discharge shall be able to be queried from the battery module. The battery may not be contained within the headset but may be connected to the headset, e.g. via an extension cable. Several methods can be used to charge the battery as well as communicate to the outside devices. The headset may receive both the power required to charge the battery as well as the external communication channel in a non-wired way. As for the charging of the battery a non-wired method can be used, such as inductively coupling power from a docking station to the device; as for the communication channel a typical 802.11, 15, 16 or 20 Wi-Fi communication channel may be used. If the headset is desired to be able to operate in a stand-alone manner, it may require a certain amount of memory in order to hold the necessary content required for each restorative health and wellness application. The headset may have a memory expansion port to utilize additional capacity if needed. The user may interact with the system via a touch pad interface located on the surface of the headset or push buttons, or a sensor array on the front of the headset may be configured to measure and track hand gestures for interacting with the device. The system may not require an external interface as just pointing the headset in a particular direction to highlight an actionable button and dwelling or nodding or some other head based gesture may be used to select an item in the immersive environment system display. If the headset is a networked based device, the headset may contain a GPS location sensor so that the learning algorithms can use this additional information when optimizing an individual's parameters. For example, GPS information from the headset may be used to determine if the user is at home or away and using this information to gain an understanding of the environment the user is currently being subjected for example a lounge at an airport located in a different time zone from their home base. In addition, this information may generate a geographic based network of users and stressors and the system may utilize the resulting information to enhance the performance of the headset. The system is configured for restorative health and wellness applications by using a number of sensors and actuators, which may be integrated into the headset or interfaced to the headset. Sensors and actuators that are not integrated into the headset can communicate with the processing unit of the headset via a wireless interface. A different wireless protocol may be used for these devices than the one used for the headset to communicate to the outside world. A communication protocol that may be used includes Bluetooth or ZigBee. The headset may be headphones solely providing audio signals to the user, and/or may include a video display based actuator. Depending on the needs of the user, the audio signals provided to the user may be configured to provide a surround sound immersive experience. Similarly, a video display included in the headset may be configured as a single display module or a dual display module for providing a better immersive environment. The illustrative headset includes an audio actuator assembly to ensure that the user is able to focus his or her hearing on the audio signals in an optimum manner. The audio actuator may be utilized to assist in the creation of the immersive environment experience as well as cancel out external noise sources in both a passive and active manner. Some versions of the system are configured to have various audio filters that can be easily changed/modified to ensure that the appropriate focus is achieved to meet the needs of the user. There are a number of other methods of achieving a focused audio signal for the user of the headset, for example having preconfigured headset assemblies with various degrees of corrective audio technology installed or pre-distorting the actual audio signal to compensate for the individual's audio characteristics. Similarly, in some embodiments, the headset includes an optical assembly to ensure that the user is able to focus his or her vision on the display in an optimum manner. Some versions of the system are configured to have various lens inserts or lens overlays that can be easily swapped to ensure that the appropriate focus is achieved to meet the needs of the user. There are a number of other methods of achieving a focused image for the user of the headset, for example having preconfigured headset assemblies with various degrees of corrective vision installed or pre-distorting the actual image to compensate for the individual's vision characteristics. The headset may offer a bypass mode where the internal electronics are bypassed and readings from the sensors, and content to the display and audio channel are provided to and by an outside device, for example a portable computer or a smartphone.

In at least some embodiments, the headset can be utilized by the individual in a standalone manner during the restorative health and wellness sessions, but it is also recognized that the headset needs to also be able to interact with the outside world. As such, several pathways can be utilized for this communication. One method is a direct connection of the headset to a wireless router to the Internet. An advantage of the direct connection is that it does not require any additional hardware beyond interfacing to a wireless network but it would than put some additional computational constraints on the headset if there was a desire to extract parametric data from the sensor/actuator signals prior to being sent for long term storage. One method to overcome this is to send the entire set of data to an intermediary server connected to the Internet that can preprocess the sensor and actuator data sets prior to forwarding them to a long term storage data base. Another communication method is to connect the device to a personal computer/laptop and run an application to synchronize the data and parameter set and then use the personal computer/laptop to forward the necessary information to the Internet. The same can be done with a mobile communication device like a smart phone. In some versions, a docking station can be configured to handle the communication requirements and synchronization along with providing a place to store the headset when not in use. Any one or a combination of these communication pathways may be used in order to configure the headset to communicate with the outside world.

Connectivity and information transfer of the data gathered from the headset to the Internet is advantageous as it one way that this data gathered from a particular headset can be incorporated in the database containing the data from other headsets for parameter optimization of various applications. For example, sleep has parameters that are highly correlated to stress, anxiety, blood pressure and the like. By being able to take into account these additional data sets, it enables additional degrees of freedom in obtaining optimum results. As such, the device has several ways to interact with the Internet. The unit can directly connect to the Internet via a Wi-Fi router; or the unit may connect to a network through a mobile device like a phone or tablet, along with the possibility of connecting via a personal computer or laptop. Beside the headset being able to both send and receive data from the Internet, the system can be configured so that other 3rd party mHealth monitoring devices can transfer their data sets to the headset or their external database can be accessed to be included as part of the comprehensive parameter set. The data from these third party mHealth-monitoring devices may be stored in the Raw Data Sets database along with the data generated from the community of users of the headset. This Raw Data Sets database would be able to be used by either internal or external groups to investigate not only the creation of enhanced restorative health and wellness algorithms and parameter sets but also for data mining purposes. A particular example of data mining might be to look at what if type questions about how various user based demographics respond to certain stimuli or how environmental events are impacting certain populations differently.

Alternatively or in addition to gathering information about the user, the system may allow the user to set his or her own personal restorative health and wellness priorities and track not only their results but also the results of their friends and community to provide an additional level of encouragement to promote continued adherence of use. To do this, the system may provide a user account profile page on a restorative health and wellness community forum. As the user progresses through a restorative health and wellness control loop, the device can take the qualitative/quantitative measurements of each individual's user state indicators (e.g. physiological parameters) and through a customized algorithm for each health and wellness metric determine a quantitative result for a particular parameter. An example of how this might work for sleep would be to look at time to fall asleep, duration of sleep, amount of slow wave sleep, total REM time, number of disruptions during the night, within-night recovery in autonomic function (e.g., percentage increases in heart rate variability, rate of change in heart rate, decreases in the rate of heart rate burst) and from that provide a weighting function to establish a total sleep quality score. The weighting function may prioritize the achievement of normative values for one of multiple sleep and sleep-related parameters (e.g., sex-, age- and weight-matched amount of slow wave sleep, percentage of sleep fragmentation, heart rate values in non-rapid-eye-movement sleep) at any specific time point in which the user does not achieve the desired or expected value, which may be based on scientific literature. For an example, in an individual with insomnia complaints, the weighted function may prioritize "insomnia-specific known altered features" to establish a total sleep quality score, such us the amount of slow wave sleep (usually suppressed in individual with insomnia). In addition to this score, the system can use e.g. a rule-based approach to provide a level of guidance to the user as to what steps can be taken to improve the user's particular score. For example, for an individual who only sleeps 4 hours a night and goes to bed at 2 am and sleeps until 6 am, the device might suggest that the user try going to bed a little earlier as their overall quantity of sleep is limiting their ability to feel rested during the day. Along with the system providing recommendations, a community forum can be an outlet for individual users to share their thoughts and experiences on what has helped them achieve their goals along with tracking their friends or colleagues. For example, an individual might want to post their restorative health and wellness regimen and obtain comments from the community as to what they might suggest for improvements. In addition, members of the community might look at what has been posted by others in the community to help in constructing their own personalized health and wellness plans. Beyond just looking at suggestions and tips from each other, versions of the system provide an area where words of encouragement or in particular recognition awards can be made to the various friends or followers of a particular individual for personal achievements. The forum may be focused on an individual's achievements or offer a way for its members to form teams and set goals for the team to enhance their prolonged compliance to the headset.

Now referring to FIG. 1, a drawing depicting an immersive environment system for the use of restorative health and wellness applications with sensor based inputs, communications based devices and actuator based outputs is shown, 100. The individual 111 would place on the face a headset, 112. This headset 112 interfaces with a variety of different sensors 120. As noted above, in some embodiments, the headset 112 is a symbolic representation of one or more displays, acoustic speakers, and other actuators that create the immersive environment for the user.

The sensors 120 can be integrated into the headset 112 or connected to the headset 112 in a wireless manner. These sensors 120 can be singular in use or multiple. A basal metabolic rate sensor, 121, can be used for detecting caloric burn in order to help with the individual manage their weight. An EEG sensor, 122, can be used to capture and measure brainwaves to monitor states of arousal. For example, insomniacs are characterized by an elevated state of arousal (e.g. high heart rate, elevated high frequency electroencephalographic activity). An EMG sensor, 123, is able to monitor muscular activity to, for example, detect an individual going into a state of rapid eye movement sleep. A camera, 124, is configured to record activities going on around the user as well to alert them if they are about to be disturbed or to enable them to interact with individuals without needing to take off the headset. A microphone, 125, is configured to sense audio signals to be used with either trying to cancel out the background noise of the environment or allow the user to interact with the environment while still wearing the headset. An accelerometer, 126, is included as one of the potential sensors for measuring the individual's head position/orientation as well as movements like respiratory if worn on the chest. The incorporation of a temperature sensor, 127, can be used to monitor and individual's temperature or that of the outside environment. A light sensor, 128, is configured to provide information about the condition of the outside environment to ensure that the settings of the headset are adjusted appropriately e.g. for the ambient lighting conditions. A blood pressure sensor, 129, may be configured to continuously monitor the individual instantaneous blood pressure. An EKG sensor, 130, is configured to measure the user's heart rate and may be configured to detect potential anomalies in the heart rate as well. A respiratory sensor, 131, measures the user's respiratory rate and depth. A humidity sensor, 132, is used to measure the user's skin moisture level. A CO2 sensor, 133, can be used to measure the gas composition of the user's breath. A SpO2 sensor, 134, is used to measure the user's blood oxygenation level. A pH sensor, 135, can be used to measure the acidity of the saliva in the user's mouth. A global positioning sensor (GPS), 136, is also able to track the individual's geographic location. Each of these sensors, 120, either used in sets or individually has the ability to measure physical properties of the individual or their surroundings and their signals are used to modulate a set of actuators, 150, to assist in providing the user of the headset 112 an optimum restorative health and wellness experience. It should be understood that embodiments of the disclosed technologies may include various different combinations of these sensors and not all of the above sensors are required in all embodiments. Further, some embodiments may include other types of sensors not discussed above.

The actuators, 150, are components of the immersive environment system that provide various aspects of the immersive user experience by producing outputs, which are received by the user. The actuators 150 are configured to produce outputs with the purpose of modulating one or more control paths in order to impact one or more aspects of the user's overall well-being. A speaker, 151, is configured to drive signals to the user's auditory senses. A video display, 152, presents outputs to interact with the user's visual senses. The system may interact with the user's touch sense through outputs generated by a vibrational device, 153. An electro shock device, 154, may be configured to generate outputs to interact with the user's nervous system. A thermal generation device, 155, is configured to generate outputs to interact with the temperature system of the individual. A chemical sent delivery device, 156, produces outputs to interact with the olfactory of the user of the headset. A light generation device, 157, is configured to produce outputs to stimulate the user's visual system similar to that of the video display, 152.

The headset, 112, communicates with the user via communication devices 140 that includes a user interface, 141. This user interface 141 allows the user of the headset, 111, to configure and start the desired restorative session and interact with other capabilities of the headset. Along with a user interface, 141, the headset has a wireless communication capability, 142. The wireless communications system, 142, may be divided into two separate systems. For example, one system can be configured in a low power format to communicate with the sensors, 120, or actuators, 150, which are not directly connected to the headset, 112, while another wireless path communicates with the outside world (and may require higher bandwidth as well as more power to achieve the desired performance).

Figure 2:
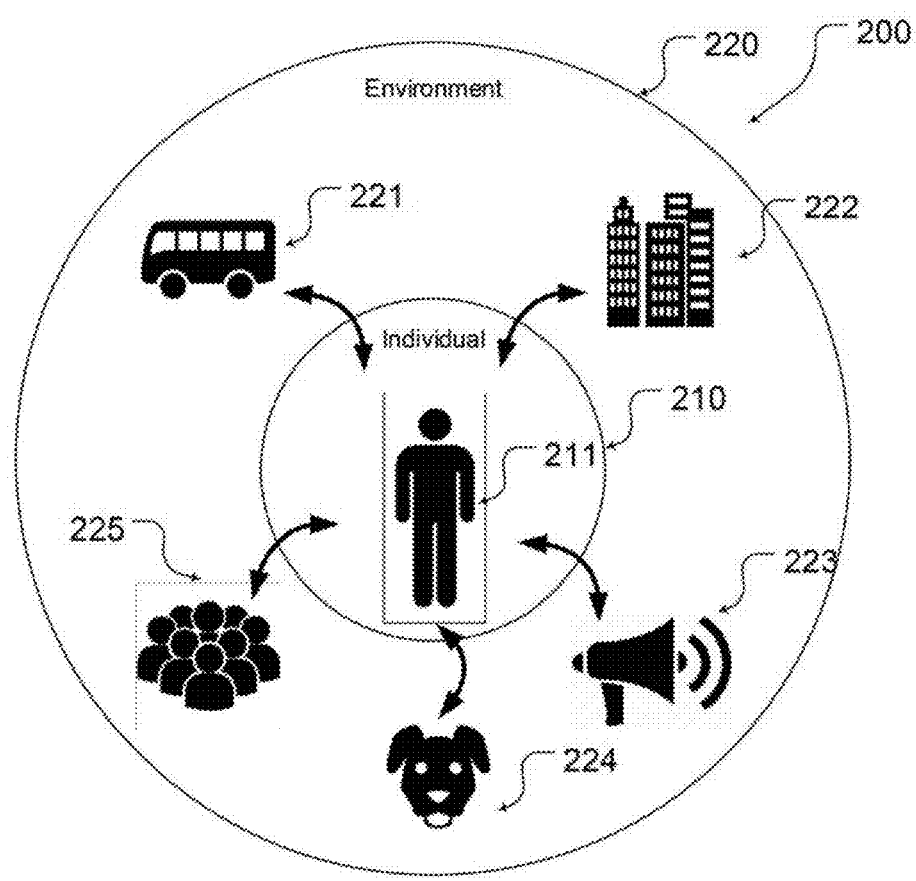
FIG. 2 is a simplified drawing of an individual, indicators of his or her overall restorative health and wellness, and the individual's interactions with the environment.

Now referring to FIG. 2, a drawing depicting an individual and their overall restorative health and wellness being impacted as well as interactions with their environment, 200. The individual's personal space, 210, is the immediate/close surroundings of the individual, 211, while the environment, 220, represents items that have the potential to modify the individual's well-being. Some of the potential environmental stressors include traffic, 221. The individual's location, 222, can provide stresses; for example, a city might have limited exposure to trees as well as sunlight. General noise, 223, of a large city or machinery can also result in modification of an individual's overall wellbeing. Animals, 224, and the noise they make, the allergens the expose the individual, 211, with that result in a reaction and the anxiety they can cause all have psychophysiological impacts on the individual, 211. Beyond just the general environmental stressors, there is also those interactions with people, 225. These interactions may be with strangers, groups, family members, business colleagues and the like.

Figure 3:
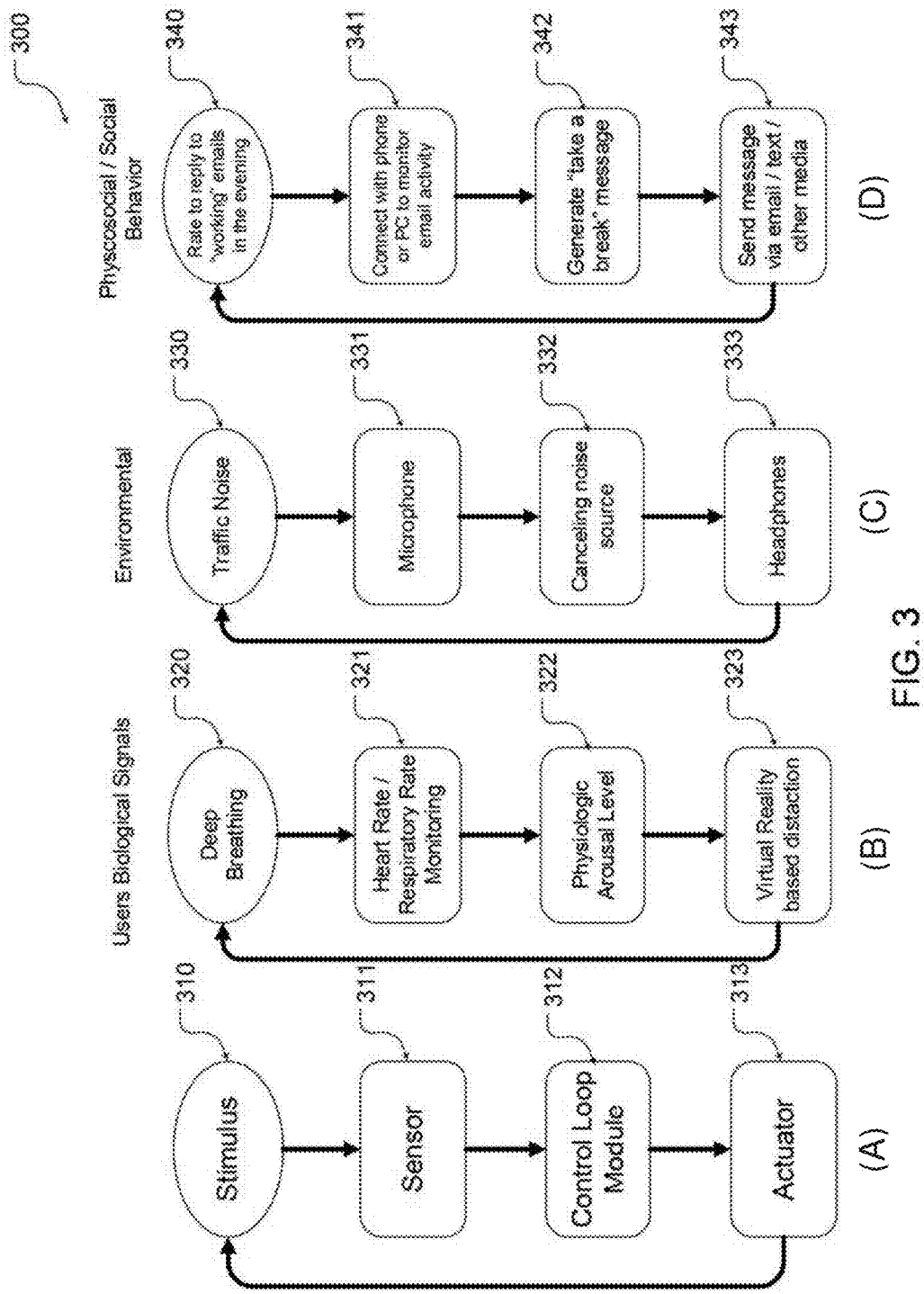
FIG. 3 depicts simplified flow diagrams of examples of a feedback loop.

Now referring to FIG. 3, a flow diagram of a feedback loop and several examples are depicted, 300. In Section (a) of FIG. 3, one or more sensors 311, measures one or more stimuli, 310. The resulting signal generated by the one or more sensors 311 is input into a control loop module 312. The control loop module is a computing device that executes one or more algorithms to generate the appropriate drive signal or information for the one or more actuators 313, in order to modify the stimuli 310, in the desired manner. That is, the control loop module 312 uses the advanced analytic techniques described here to determine an optimized set of parameters (i.e., the drive signal) to create the immersive environment for the individual.

For example, in some embodiments, the one or more sensors 311 may include heart rate sensors. The heart rate measurements from the heart rate sensors are input into the control loop module 312. The control loop module 312 uses the physiological properties of the individual measured by the heart rate sensors and advanced analytic techniques to determine an audio signal to play for the individual. Once the control loop module 312 determines a set of parameters to drive the actuators, the control loop module 312 will instruct the one or more actuators 313 accordingly to create the immersive environment. For example, the control loop module 312 may instruct the one or more actuators 313 to play a sinewave tone into both ears. The individual's heart rate is continually measured via heart rate via sensors 311 while the sinewave tone is played into both ears, and after a fixed time the frequency is tuned upward. If the heart rate increases, the control loop module 312 may determine to adjust the frequency lower. If the heart rate decreases as desired, this information is used by the control loop module 312 to guide further timed probing of lower frequencies, each time testing for heart rate effect. Families of such algorithms run by the control loop module 312, running in parallel or in sequence, can probe physiologic responses to tone lengths, harmonic contents, frequencies, envelopes, and other modifiable aspects to build a model to later synthesize optimally relaxing audio content. At a higher level, simply probing the physiologic responses to various musical passages can be used to determine, by the control loop module 312, which forms of music yield the best relaxation effect for each user.

Additional examples are depicted with respect to Sections (b), (c) and (d) of FIG. 3 are generally described below. Section (b) in FIG. 3 represents the feedback loop as it relates to an example in which the user's biological signals are monitored to induce sleep, with the stimulus, 310, being represented by deep breathing, 320. The sensor, 311, detects the user's heart rate and/or respiratory rate, 321. The control loop module, 312, processes the stimulus data (e.g. heart rate, respiratory rate data) and executes one or more algorithms to determine the user's level of physiologic arousal level, 322. The actuator, 313, may execute one or more algorithms in order to determine and generate an appropriate immersive environment based user experience, 323, based on the detected level of physiologic arousal and the stated goal of promoting or inducing sleep.

Section (c) of FIG. 3 represents the feedback loop in an example that relates to the user's environment for inducing sleep, with the stimulus, 310, being represented by traffic noise, 330. The sensor, 311, represented by a microphone, 331, the control loop, module 312, represented by a noise canceling source, 332, and the actuator, 313, represented by headphones, 333. In some embodiments, canceling the noise source 332 includes at least one of modifying, decreasing, canceling, drowning out, or filtering the offending noise 330.

Section (d) in FIG. 3 represents the feedback loop in an example that relates to the user's psychosocial/social behaviors and how these behaviors induce sleep, with the stimulus, 310, being represented by rate to reply to "working: emails in the evening," 340. The sensor, 311, being represented by connection with the phone or PC to monitor email activity, 341, the control loop module, 312, being represented by the generation of a "take a break" message, 342, and the actuator, 313, being represented by sending a message to the user via email/text/or other media, 343.

Figure 4:
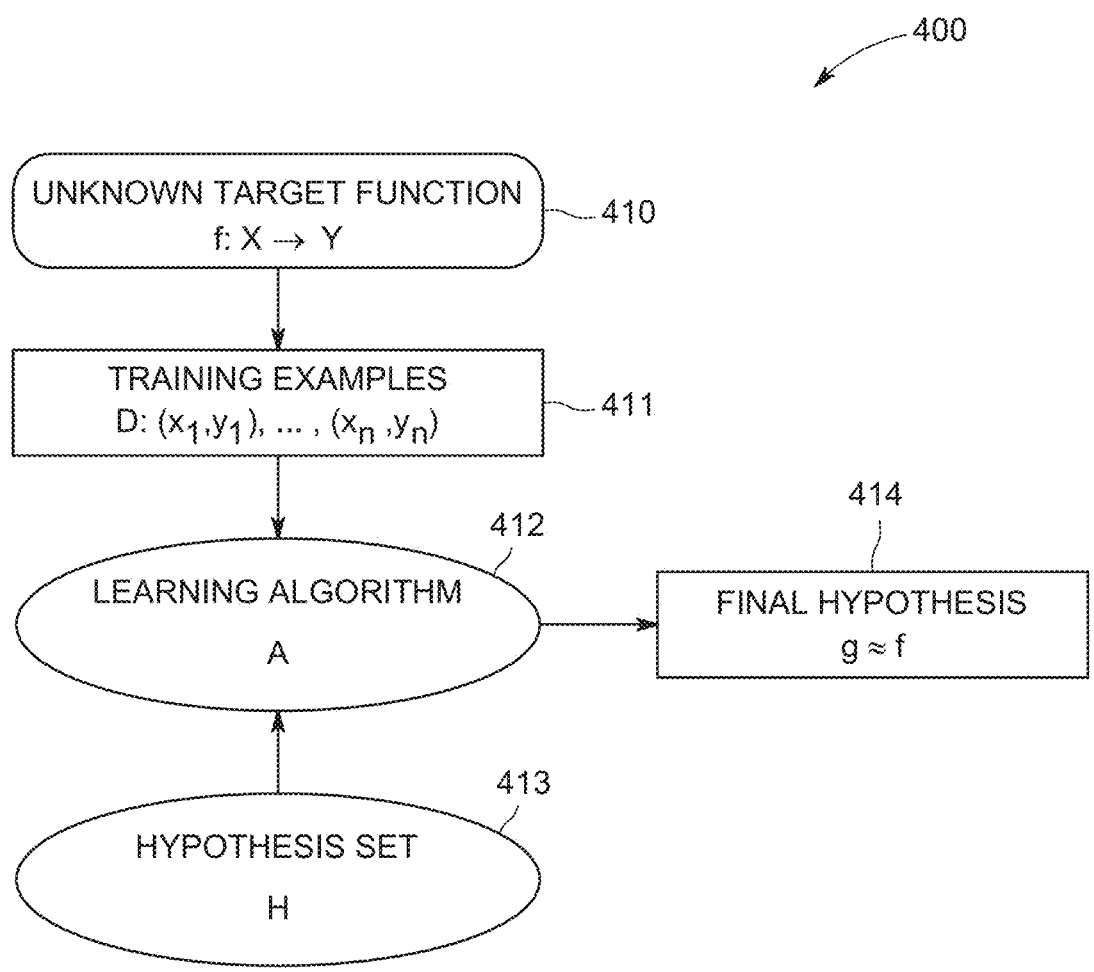
FIG. 4 is a simplified flow diagram of a machine learning algorithm.

Now referring to FIG. 4, a flow diagram of a machine learning algorithm is shown, 400. The illustrative algorithm is configured to take an unknown target function, 410, that maps a set of measurements/information that can be discrete like male/female or continuous like weight and maps it to a desired set of outputs that can also be discrete or continuous in nature. In order to get a good estimate of the unknown target function it is desired to have a set of training examples, 411. These training examples, 411, include a set of data that has been collected along with the appropriate actions that needed to be taken. This is a type of supervised machine learning. Unsupervised machine learning techniques may be used, alternatively or in addition to supervised machine learning techniques. In supervised machine learning the training examples, 411, may be segmented into two sets: one set for training and one set for testing of accuracy of the learning algorithm, with the goal of optimizing the accuracy of the testing set. The algorithms may start with a base hypothesis set, 413, and the training example set, 411, is used to modify the hypothesis set, 413, based on a quality metric function until a stable point is reached for the learning algorithm, 412. As additional training examples, 411, are collected the learning algorithm, 412, can continue to be refined. Once the learning algorithm, 412, is completed the final hypothesis, 414, results, with the final hypothesis, 414, function g closely matching that of the unknown target function, 410, f. In some embodiments, the machine learning algorithm can be performed in the cloud via a distributed system. In some embodiments, the machine learning is used to optimize the control loop that controls the immersive environment and associated actuators to produce the desired immersive environment.

Figure 5:
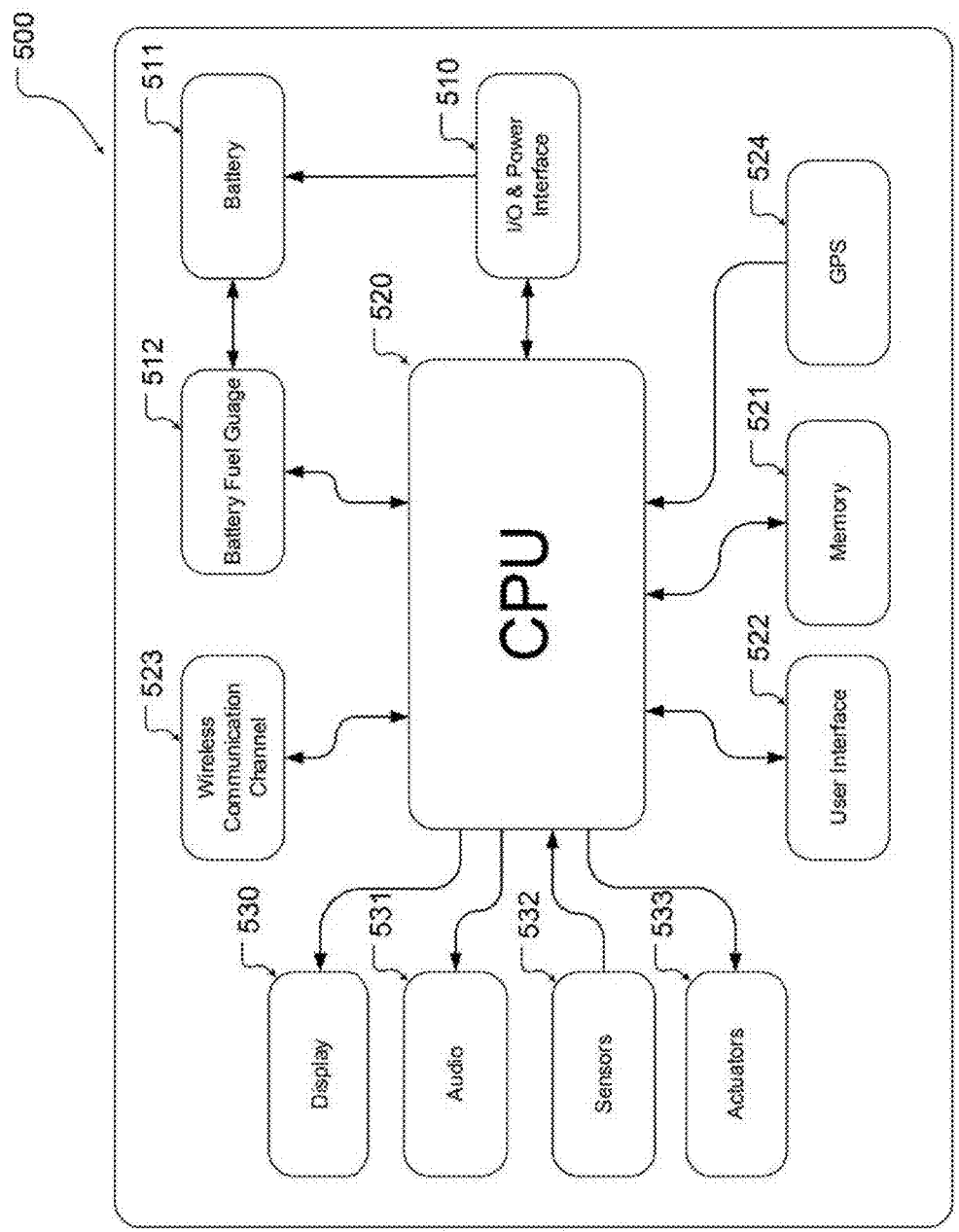
FIG. 5 is a simplified block diagram of an embodiment of a restorative health and wellness immersive reality headset.

Now referring to FIG. 5, a block diagram of a restorative health and wellness immersive reality headset is shown, 500. This block diagram, 500, depicts items that are included in the illustrative headset. In some versions, the number of the items may vary, and items may be removed or substituted for alternative technologies and the overall functionality may remain constant. For example, the Global Positioning System (GPS), 524, module may be substituted or removed by relying on the wireless communication channel, 523, to get general position data.

The central architecture of the block diagram, 500, includes a Central Processing Unit (CPU), 520. This CPU, 520, may function as the main communication, processing, and control unit for the entire headset. The CPU, 520, has the ability to interface for power as well as communications through the I/O & power interface, 510. This I/O & power interface, 510, can be implemented in a wired or a wireless manner. For example, it would be straightforward to transfer power to the headset by inductive coupling if wireless is desired. The communications channel can be accomplished via a USB (Universal Serial Bus) connection in a wired configuration or employ the wireless communication channel, 523, for wireless. The I/O & Power Interface, 510, is used to charge the battery, 511. The battery, 511, is monitored by the battery fuel gauge, 512 to keep track of the overall status. The battery fuel gauge, 512, may be configured to keep track of the charge status, total capacity, temperature, voltage, and the like. The wireless communication channel, 523, serves several purposes for the headset, 500. This wireless communication channel, 523, may be configured into two separate channels. One for low bandwidth low power communications and one for high bandwidth and higher power communications. A typical low power channel might be Bluetooth, while a higher power and higher bandwidth one might be 802.11. The low power channel can be used to interact with both on-body as well as off-body sensors and actuators, while the high power channel is typically used for communications with other mobile devices, Wi-Fi networks and the like. At least a single integrated display, 530, is incorporated into the headset, 500. More than one display, 530, may be used. For example, given some of the form factor constraints it might be advantageous to use two displays to interact with the user's eyes. The display can utilize a number of technologies like LCD (liquid crystal display), OLED (organic light emitting diode) and the like. The display is configured to provide sufficient fidelity to create the perception of a natural immersive environment from the standpoint of resolution, dynamic range, color gamut saturation level, response time, and the like. The display, 530, may be configured to minimize power needs. As for the audio, 531, of the headset, this actuator is configured to provide an immersive natural environment to the user and minimize external noise based distractions. In order to accomplish this the audio, 531, actuator is constructed to be able to utilize noise canceling algorithms of interference signals obtained from the other sensors, 532, connected to the headset, 500. This audio, 531, channel is of additional speakers of the audio path may not be in contact with the ears but may be contained within the headsets, 500, visual enclosure to be able to provide an additional depth of reality related to producing directional pressure waves to excite the touch receptors of the users face. The sensors, 532, that work with the headset, 500, can be both incorporated into the headset, 500, as well as interfaced through the wireless communication channel, 523. A non-limiting sample of the type of sensors 120 that might be used is discussed above with respect to FIG. 1. Additional actuators, 533, that work with the headset, 500, can be both incorporated into the headset, 500, as well as interfaced through the wireless communication channel, 523. A non-limiting sample of the type of actuators 150 that might be used is discussed above with respect to FIG. 1.

The headset, 500, also includes a user interface, 522, so the user of the device is able to interact and configure the headset, 500, to perform the desire functions. This user interface, 522, shall interface with the CPU, 520, to be able to received and interpret commands from the user of the headset, 500. Several types of user interfaces, 522, may be used. One of the simplest might be a touch pad connected to the side of the headset, 500, while a more complex one might be a hand gesture based sensor. The user interface, 522, may be able to utilize other types of interactions with the wearer of the headset, 500. For example, the user interface may track the user's eye motion and their blink response to work as an interface or a simple voice command based interface may be utilized. If it is desirable for the headset, 500, to be able to function as a self-contained unit, sufficient memory, 521, is configured to be available to store the necessary content. The bandwidth of the wireless communication channel, 523, may be sufficient to stream the necessary content and result in reducing the memory, 521, requirements of the headset, 500.

A number of the functions that are connected with the CPU, 520, over time might not be required to be separate modules as a higher level of integration of functionalities on a CPU module may be possible, and as such the periphery modules to the CPU, 520, of headset block diagram, 500, may not be required as their functionality may be integrated into the CPU, 520.

Figure 6:
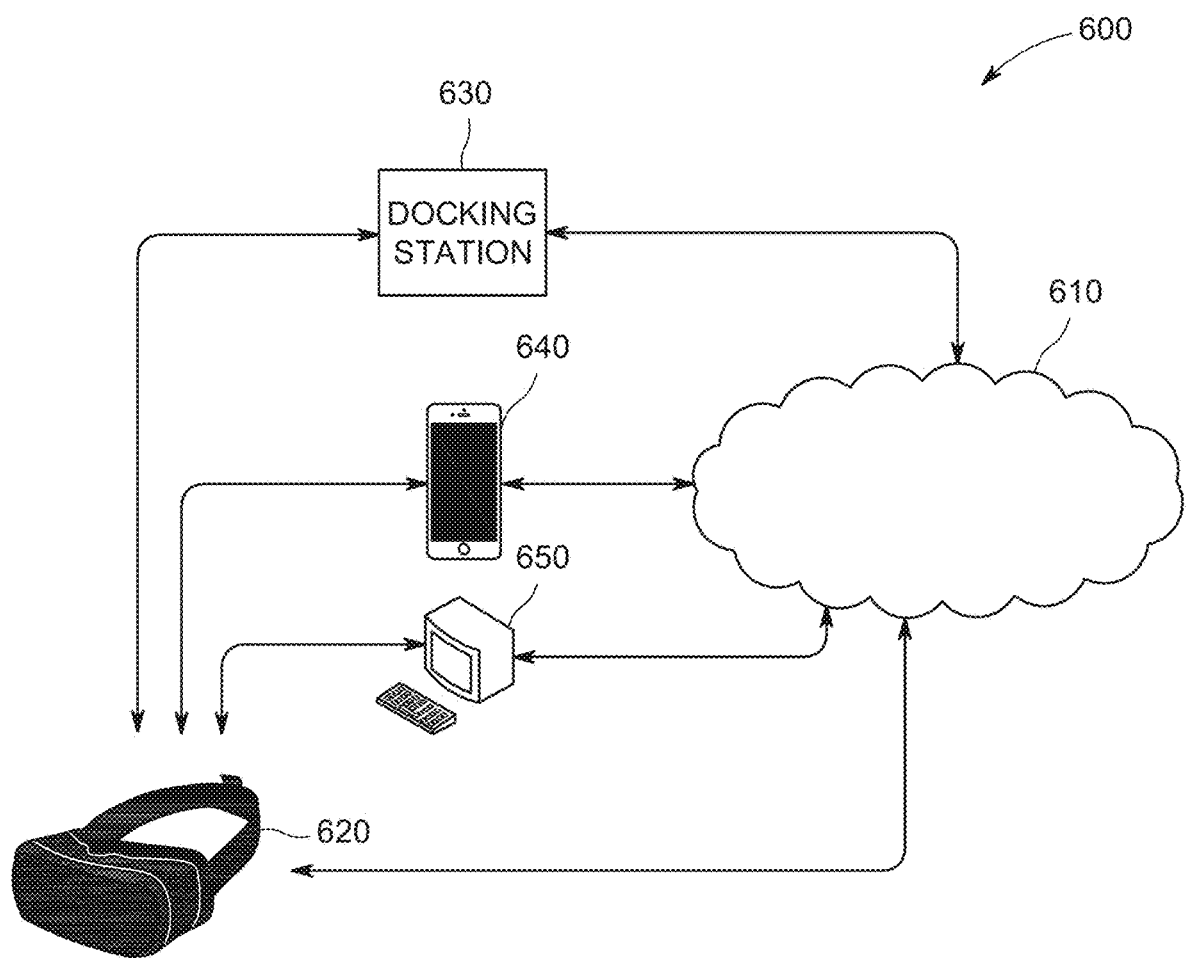
FIG. 6 is a simplified depiction of multiple communications paths that can be used with an immersive system.

Now referring to FIG. 6, a depiction of the multiple communications paths that can be used with the headset, 620, is shown, 600. The headset, 620, has several pathways that it can communicate with the cloud/Internet, 610. The most direct pathway for the headset, 620, to communicate with the cloud/Internet, 610, is in a wireless manner. Utilizing this pathway might put some additional processing constraints on the headset, 620, in which case the data may be preprocessed and then transferred to minimize bandwidth and potential storage costs. For example, the headset, 620, may transmit that data to an intermediary server connected to the cloud/Internet, 610, for preprocessing prior to being transferred for long term storage. An additional communication path between the headset, 620, and the cloud/Internet, 610, can be implemented via a personal computer/laptop, 650. This personal computer/laptop, 650, can be used not only as a bulk local storage device for additional content for the headset, 620, but also be utilized as a preprocessing engine for parametric parameter extraction purposes prior to transferring data to long term storage on the cloud/Internet, 610. An additional path that can be used for the headset, 620, to communicate with the cloud/Internet, 610, can be implemented via a mobile communications device, 640, like a smart phone or tablet. These mobile communication device, 640, can offer similar services and capabilities as those described for the previously for that of the personal computer/laptops, 650, but in addition can provided the added flexibility of access to a cellular network communication channel to the cloud/Internet, 610. One additional communication path between the headset, 620, and the cloud/Internet, 610, can be accomplished via a docking station, 630. The docking station may be configured to offer similar communications/preprocessing and bulk storage capabilities of that of the personal computer/laptop, 650. The docking station, 630, can communicate with the cloud/Internet, 610, in either a wired or a wireless manner for the purpose of data transfer.

Figure 7:
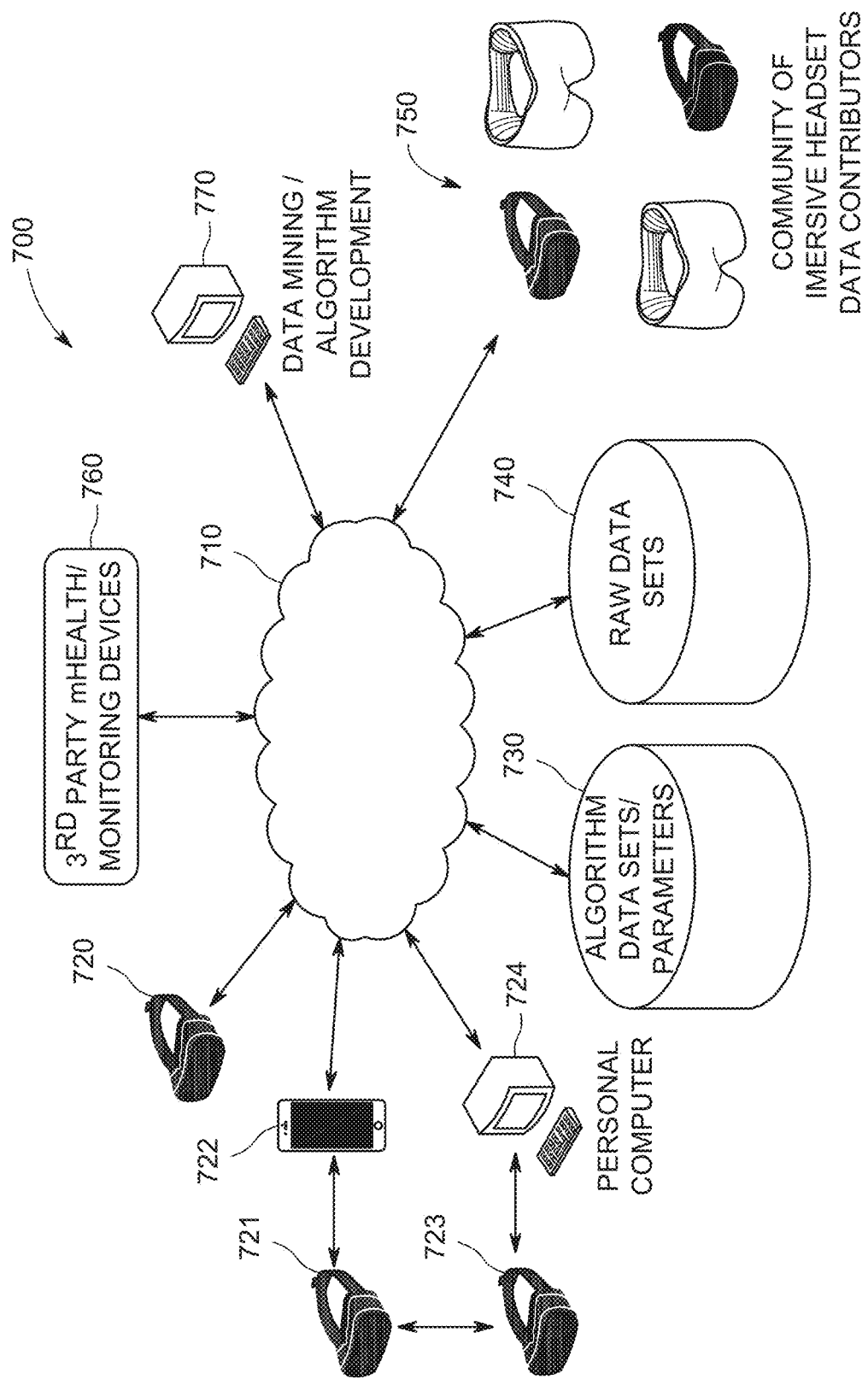
FIG. 7 is a simplified depiction of interactions of a single user headset with cloud based storage, distributed, networked community of users, and other devices.

Now referring to FIG. 7, a drawing showing interactions of a single user headset, (720, 721, 723), with a cloud based storage/distribution/networked community of users and other e.g. mHealth based devices is shown, 700. These interactions can provide the foundation for the overall interconnection of a community of users, 750, for the purpose of aggregating the readings from their sensors and actuators in a common database of raw data sets, 740, that can be used for the generation of personalized algorithms for the individuals, (720, 721, 723) to track and provide optimum settings for their restorative health and wellness needs. In some embodiments, machine learning/artificial intelligence models are trained used this aggregated data to provide a customer user-specific experience. An individual headset, (720, 721, 723), can interact with the cloud/Internet, 710, directly as shown in 720, or through a mobile communication device, 722, as shown in 721, or through a personal computer, 724, as shown in 723. In some embodiments, the headsets (720, 721, 723) can directly interact with each other through wireless or wired communications protocols. This interaction with the cloud/Internet, 710, is for the purpose of transferring data to the raw data sets, 740, and receiving algorithm data sets/parameters, 730, for optimized user settings. Beyond storing data from the community of headsets, 750, there is also the capabilities to collect parametric and raw data from the larger 3rd party mHealth/monitoring devices, 760, for storage in the raw data sets, 740, and used for algorithm data sets/parameters, 730, generation. This data can also be accessed and utilized via a data mining/algorithm development, 770, pathway for researchers to generate customized based algorithms or mine the data for additional information contained.

Figure 8:
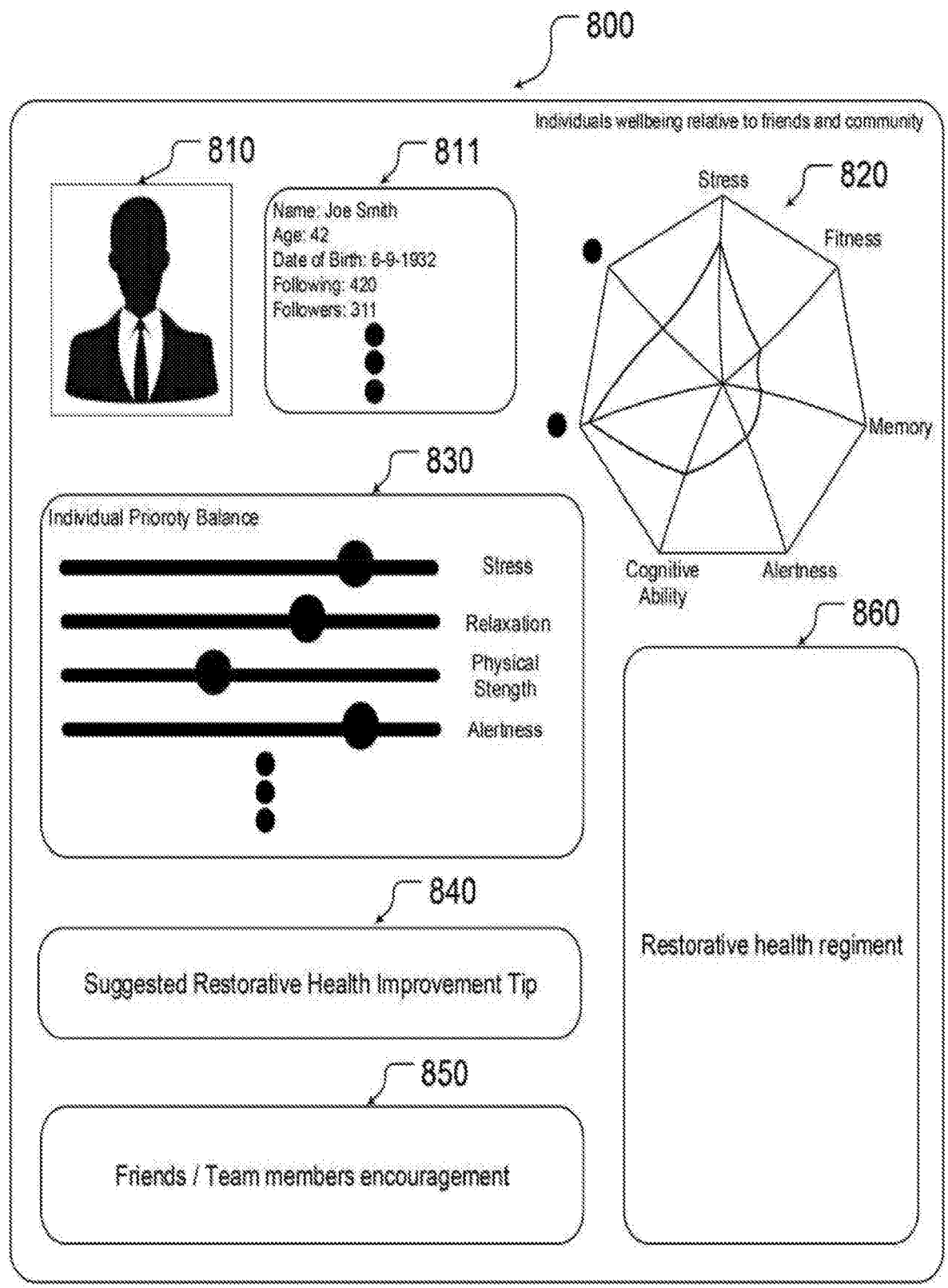
FIG. 8 is a simplified depiction of a user interface including a personal profile or community communication dashboard.

Now referring to FIG. 8, a personal profile/community communication dashboard is shown, 800. This dashboard, 800, is configured in an interactive manner where the user is easily able to customize the system to their current needs or goals. It can also be visible to friends of the use where they can interact and provide suggestions or encouragement for the user. The user may provide a picture of themselves, 810. This picture, 810, can be changed based on the user's current preferences. An example might be if the individual is suffering from lack of sleep they may have a sleepy picture shown or if they are well rested a happy alert picture of themselves is shown. It is also possible for the page to automatically modify the picture, 810, from a family of pictures to show a picture, 810, of the user that best represents their current condition. In addition to the picture, 810, a user demographic/status section can also be displayed, 811. This demographic section, 811, can contain information like name, age, date of birth, followers, number of people following, weight and the like. Some versions of the system are configured to depict the individual's overall restorative health and wellness conditions, 820, along with how they have they relate to their average state along with how they relate to the people they are following as well as their followers and individual form the greater community who have similar objectives. One way to depict this type of information in a concise and compact manner is with a bull's eye graph as shown in 820. The dashboard, 800, should also contain the ability for the individual to select their desired priority balance for health and wellness, 830. This priority balance, 830, can be used to also match the individual or suggest matches with others in the community with similar goals for trying to get better long term adherence to their health and wellness program. Based on the current condition of the user and their prior history it is also possible for a message of the day to be generated, 840, by the system to provide a suggestion or words of encouragement to the user on how they might be able to improve or maintain their current status. The system can be configured to provide an initial suggestion for an overall restorative health regimen, 860, or this section may be primarily maintained by the user so they feel a level of empowerment for their own health. This restorative health regiment, 860, section can also be a guide to others who are following the user as to what they might be able to do to improve their overall restorative health and wellness condition. Not only can followers of the user view the user's dashboard, 800, but they should also be able to post suggestions or words of encouragement, 850, to the user. This section can also be used for bulk posts to teams of users who have a common interest so posting on one individual team members page may be configured to post on all team members dashboard. The content contained on the dashboard may be limited to text or may include a full set of multimedia capabilities along with the ability to provide links (e.g. hyperlinks) to additional content.

Illustrative examples of the technologies disclosed herein are provided below. An embodiment of the technologies may include any one or more, and any combination of, the examples described below.

An immersive restorative health and wellness device with closed loop control capabilities based on physiological responses. An immersive restorative health and wellness device configured to operate in a feedback or feed forward manner. Feedback mechanisms to modulate an immersive virtual world experience.

A system configured to transform an immersive virtual world from a chaotic state to an orderly functioning state as the user responds to the system-generated restorative health and wellness user experience by aligning his or her behaviors to those behaviors that are conducive to bringing on the desired restorative health and wellness benefit.

A method to modulate the immersive virtual world intensity based on physiological responses or environmental factors. A method to modulate the immersive virtual world journey based on user compliance.

A system to utilize information obtained from sensors located in the headset 112 as the modulation input device. A system to utilize information obtained from sensors of aspects of the user's surrounding physical environment during the day as the modulation mechanism of the device (e.g. stress, commute time, social environment, average noise level, activity level).

A system configured to apply an immersive environment experience to one or more applications including: sleep and sleep disorders, Insomnia, over-active mind, jet lag, vices, smoking, sex, gambling, post-traumatic stress disorder, phobia, spiders, snakes, clowns, heights, anxiety, public speaking, strangers, mood, depression, blood pressure, chronic pain, exhaustion, mediation, prejudices, racial discrimination, sexual discrimination, age discrimination, headaches, weight control.

A system including a combination of sensors and actuators linked to an immersive environment system either directly or through a wireless communication path. The system may incorporate signals from the user's environment that are external from the user (e.g., ambient noise, rate of email responses, room temperature, overall tone of the surroundings (relaxing, stressful, chaotic, etc.) and the like.

A system to characterize health of users using responses to stimuli. The system may use different levels of stimuli, e.g. playing a tone at night to monitor the HR (heart rate) curve of response or by monitoring responses to arousals.

A system to amalgamate data readings from various other e.g. mHealth based, mobile devices being continuously gathered. (i.e., take signals from and around the user continuously (24/7) even when the restorative health and wellness headset is not being used).

The system may be implemented using: smart watch, smart phone, wrist band based device, etc.

The system may incorporate data gathered from various other e.g. mHealth based, mobile devices into the parameter set used for providing optimized restorative health and wellness based therapy.

The system may use machine learning techniques to control/regulate physiological control/set point paths.

The system may use algorithms including: decision tree learning, association rule learning, artificial neural networks, inductive logic, support vector machines, clustering, Bayesian networks, reinforcement learning, representation learning, similarity and metric learning, sparse dictionary learning, genetic algorithms, weighted combination, voting based methods, distributed dataset sharing/database for continued algorithm refinement and personalized therapeutic optimization, etc.

The system may be configured to upload restorative health/wellness data sets from the immersive environment system to the cloud (big data). The system may be configured to download new control parameters and algorithms for personalized therapeutic optimization to the users' needs but calculated across a similar population of users (big data).

The system may be configured to mine the data sets to generate custom based algorithms (big data). The system may be configured to set personal goals for the device and have the content/closed loop control algorithm be optimized based on goals via the information gathered from other users of the VR headset with non-disjoint goals (can be identical but not necessary).

The system may be configured to translate the "heath" aspects of an individual into a numeric (0% to 100%) score(s) or qualitative (terrible, bad, neutral, good, excellent) score(s) to a given health aspect: sleep, stress, fitness, alertness, functioning, balance.

The system may be implemented as a "social health" platform.

The system may further provide: goal setting, personal tracking, individual profile selection, measurement of individual with reference to community, ability to form teams for community based goals or greater adherence.

The system may incorporate t-VNS as a potential actuator for controlling sleep apnea, adverse cardiac event, seizures, mood, attention/focus, etc.

The system may be configured to use a forward looking camera and microphone to transition between an immersive environment experience and the outside world.

The system may be configured to enable the user to customize/personalize and share their immersive environment experiences with users. In some embodiments, the immersive environment for the individual is personalized based on at least one of the individual's favorite music, preferred audio tracks, pictures of importance, or sounds identified as comforting by the individual.

The system may be configured to allow users to add sprites to their immersive environment (i.e., favorite cat, lamp, pillows, bed, etc.).

The system may be configured to enable users to share their immersive environments for group support/bonding activities.

The system may be configured to sense and allow known signals for example the cry of a baby to penetrate the immersive environment experience.

The system may be configured to enable users to upload pictures of items (cat, dog, table, chair) to be converted into sprites that can be included into their immersive environment.

The system may be configured to bypass the internal system content to interface to an external content source as well as have the sensors output to the external content source for closed loop control capabilities.

The system may include a sensor/actuator section on the surface presenting to the face is removable and replaceable with a different sensor module. The interface to this module may accommodate a number of different sensor/actuator configurations.

The system may be configured to utilize a standard VR headset that interfaces to a computer or one that utilizes a smart phone device and replace the face presented gasket with one that includes physiologic sensors and actuators that can be used to feed information back to the controlling device to module the user experience in a closed loop controlled manner.

The headset device and system may be implemented as part of a broader digital health/consumer ecosystem. This may include fusing (e.g. establishing data communication between) the headset device and one or more other wearables, such as wrist-based devices, which can provide wireless input to the headset device of parameters such as heart-rate. In these embodiments, the headset device may be a relatively simple device with the ability to interface with many other devices, including consumer oriented devices as well as servers, to obtain the needed physiological measurements, data, content, and/or control signals.

A system that can use natural language voice input/output for user control of the headset configuration and/or adjustment of parameters of the user experience. In an example, a user may simply say "dim the display" or "change from a space scene to green fields of grain" as a control directive to which the system is responsive. The system may respond to e.g. speech-based natural language inputs in a dialog manner using system-generated natural language e.g. text-to-speech output.

A system for monitoring and analysis of a user's physiology. The system may be configured for detection of e.g. apnea (serious), snoring, arrhythmias, etc., or interface with existing devices that provide these capabilities. The system and/or any such devices may post sensed physiological data to the cloud (network-based storage, e.g. server devices), merely for storage or for processing by cloud-based analytical services. Results of such processing may be sent to the user's headset device or to other individuals such as health providers or emergency services.

An immersive environment system for sleep promotion, where the headset device and system are configured for use in hospitals and/or other noisy environments.

A system configured to measure and use evoked potentials to audio or visual stimuli, for example sub-perceptual stimuli, and which may gather results using ensemble averaging or other techniques to improve SNR (signal to noise ratio).

A system configured with variable-depth acoustic noise cancelation capabilities. The system may, for example, gradually "fade-out" environmental sounds (like in an airplane) as the system detects the user exhibiting physiologic signs of falling asleep. Conventional noise canceling techniques can be used to implement the fade-out. The system may then reverse the fade-out as the system detects the waking or, the system detects certain audio segments, for example, a flight attendant says, "Excuse me, sir."

A system that can store or obtain the content used to provide the user experience from the cloud. When the system is "off-grid" the system may be configured to upload local content.

A system configured for use aboard a vehicle, such as a car, bus, train, or an airplane in-flight. Use of the system may be tied to e.g. loyalty plans such that the headsets are automatically (if prepaid) allowed to join in-vehicle or in-flight Wi-Fi services (and still use some reduced bandwidth remote processing power).

The above examples, details, and scenarios are provided for illustration, and are not intended to limit the disclosure in any way. Those of ordinary skill in the art, with the included descriptions, should be able to implement appropriate functionality without undue experimentation. References in the specification to "an embodiment," "version," etc., indicate that the embodiment described may include a particular feature, structure, or characteristic, but every embodiment may not necessarily include the particular feature, structure, or characteristic. Such phrases are not necessarily referring to the same embodiment. Further, when a particular feature, structure, or characteristic is described in connection with an embodiment, it is believed to be within the knowledge of one skilled in the art to affect such feature, structure, or characteristic in connection with other embodiments whether or not explicitly indicated. Embodiments in accordance with the disclosure may be implemented in hardware, firmware, software, or any combination thereof. Embodiments may also be implemented as instructions stored using one or more machine-readable media, which may be read and executed by one or more processors. A machine-readable medium may include any mechanism for storing or transmitting information in a form readable by a machine. For example, a machine-readable medium may include any suitable form of volatile or non-volatile memory. Modules, data structures, function blocks, and the like are referred to as such for ease of discussion, and are not intended to imply that any specific implementation details are required. For example, any of the described modules and/or data structures may be combined or divided into sub-modules, sub-processes or other units of computer code or data as may be required by a particular design or implementation. In the drawings, specific arrangements or orderings of schematic elements may be shown for ease of description. However, the specific ordering or arrangement of such elements is not meant to imply that a particular order or sequence of processing, or separation of processes, is required in all embodiments. In general, schematic elements used to represent instruction blocks or modules may be implemented using any suitable form of machine-readable instruction, and each such instruction may be implemented using any suitable programming language, library, application programming interface (API), and/or other software development tools or frameworks. Similarly, schematic elements used to represent data or information may be implemented using any suitable electronic arrangement or data structure. Further, some connections, relationships or associations between elements may be simplified or not shown in the drawings so as not to obscure the disclosure. This disclosure is to be considered as exemplary and not restrictive in character, and all changes and modifications that come within the spirit of the disclosure are desired to be protected.

The invention claimed is:

1. A restorative health and wellness system that provides an immersive environment, comprising:
   one or more sensors configured to measure physiological properties of an individual and/or properties of surroundings of the individual;
   one or more actuators configured to create the immersive environment for the individual, wherein the immersive environment is an environment that attempts to improve sleep quality or relaxation by immersing the individual in an optimal environment;
   a control loop module configured to receive and analyze input from the one or more sensors, and to provide information to the one or more actuators to create the immersive environment for the individual; and one or more communications devices configured to facilitate communications between the one or more sensors, the one or more actuators, and the individual, wherein the one or more actuators dynamically create or adjust the immersive environment based on at least one of (A) the physiological properties of the individual measured by the one or more sensors or (B) the properties of the individual's surroundings measured by the one or more sensors, and pre-determined health and wellness goals set for the individual.

2. The restorative health and wellness system of claim 1, wherein the optimal environment in which the individual is immersed in is one that attempts to induce increased relaxation for that individual or generates a higher sleep quality score.

3. The restorative health and wellness system of claim 2, wherein the sleep quality score is determined from at least one of the measured physiological properties and other properties including input from the individual, and the properties of the individual's surroundings, and includes at least one of a time to fall asleep, a duration of sleep, a total rapid eye movement (REM) sleep time, slow wave sleep time or a number of disruptions during night time.

4. The restorative health and wellness system of claim 1, wherein the properties of the individual's surroundings include signals from other individuals that are close in proximity to the individual.

5. The restorative health and wellness system of claim 1, wherein the one or more sensors are at least one of one or more sensors integrated into an immersive environment headset worn by the individual, connected to the immersive environment headset in a wired or wireless manner, facial sensors or configured to be disposed on or about the individual.

6. The restorative health and wellness system of claim 5, wherein the one or more sensors configured to measure physiological properties of an individual include at least one of a basal metabolic rate sensor configured to detect caloric burn, and EKG sensor configured to measure heartrate, an EEG sensor configured to capture and measure brainwaves to monitor states of arousal, an EMG sensor configured to monitor muscular activity to detect an individual going into a state of rapid eye movement (REM) sleep, bioimpedance sensor to measure impedance cardiography, or an accelerometer configured to measure the individual's position and movement.

7. The restorative health and wellness system of claim 5, wherein the one or more sensors configured to measure the properties of the individual's surroundings include at least one of a camera, a microphone, a temperature sensor, or a light sensor, configured to provide information about a condition of the environment to ensure that settings of the headset are adjusted appropriately for ambient conditions.

8. The restorative health and wellness system of claim 1, wherein the one or more actuators include a speaker configured to output signals to auditory senses of the individual.

9. The restorative health and wellness system of claim 8, wherein the one or more actuators further include at least one of a video display, a vibrational device, an electro shock device, a thermal generation device, a chemical sent delivery device, or a light generation device.

10. The restorative health and wellness system of claim 1, wherein the immersive environment for the individual is based on at least one of the individual's favorite music, preferred audio tracks, pictures of importance, or sounds identified as comforting by the individual.

11. The restorative health and wellness system of claim 1, wherein the one or more actuators dynamically create or adjust the immersive environment further based on an optimized set of control parameters used to drive the one or more actuators determined through a statistical analysis of measurements taken by the one or more sensors and wherein the optimized set of control parameters determined through the statistical analysis of measurements taken by the one or more sensors is based on historical data collected with respect to the properties of the individual's surroundings or information about the individual.

12. The restorative health and wellness system of claim 11, wherein the statistical analysis of measurements taken by the one or more sensors includes at least one of predictive modelling, machine learning, or data mining that analyzes current and historical facts.

13. The restorative health and wellness system of claim 11, wherein the optimized set of control parameters determined through the statistical analysis of measurements taken by the one or more sensors is based on the use of aggregated data to train a machine learning model to provide a custom user-specific experience, the aggregated data including properties measured from other individuals and retrieved from one of a cloud computing environment and one or more external devices.

14. The restorative health and wellness system of claim 11, wherein the statistical analysis of measurements taken by the one or more sensors include at least one of using of rule-based models where the rules may be set based on personal preferences of the individual or preferences of individuals in surroundings with common characteristics, or using if-then logic.

15. The restorative health and wellness system of claim 1, wherein the dynamically created or adjusted immersive environment induces an increased sense of presence in the individual, wherein the increased sense of presence in the individual can be measured by the one or more sensors configured to measure physiological properties of an individual.

16. A restorative health and wellness system that provides an immersive audio environment, comprising:

one or more sensors configured to measure physiological properties of an individual and/or audio signals from an individual's environment;

one or more audio actuators configured to create the immersive audio environment for the individual, wherein the immersive audio environment is an environment that attempts to improve sleep quality or relaxation by immersing the individual in an optimal audio environment;

a control loop module configured to receive and analyze input from the one or more sensors, and to provide information to the one or more audio actuators to create the immersive audio environment for the individual; and one or more communications devices configured to facilitate communications between the one or more sensors, the one or more audio actuators, and the individual, wherein the one or more audio actuators dynamically create or adjust the immersive audio environment based on at least one of (A) the physiological properties of the individual measured by the one or more sensors or (B) the audio signals from the individual's environment measured by the one or more sensors, and pre-determined health and wellness goals set for the individual.

17. The restorative health and wellness system of claim 16, wherein the optimal environment in which the individual is immersed in is one that induces increased relaxation or generates a higher sleep quality score.

18. The restorative health and wellness system of claim 17, wherein the sleep quality score is determined from the measured physiological properties and properties of the individual's surroundings and includes at least one of a time to fall asleep, a duration of sleep, a total rapid eye movement (REM) sleep time, slow wave sleep time or a number of disruptions during night time.

19. The restorative health and wellness system of claim 16, wherein the audio signals of the individual's environment include signals from other individuals that are close to the individual.

20. The restorative health and wellness system of claim 16, wherein the restorative health and wellness system uses ensemble averaging to improve SNR (signal to noise ratio) in modifying, decreasing, canceling, drowning out, or filtering the audio signals from the individual's environment.

21. The restorative health and wellness system of claim 16, wherein the restorative health and wellness system is configured with variable-depth acoustic noise cancelation capabilities and gradually "fades-out" environmental sounds if the system detects positive effects on the measure physiological properties of the individual as the environmental sounds are being gradually faded-out.

22. A computer implemented method for a restorative health and wellness system that provides an immersive environment, the method comprising:
receiving, from one or more audio sensors, audio signals from an individual's environment;
receiving, from one or more physiological sensors, physiological properties measured from an individual;
receiving and processing the physiological properties and audio signals using a control loop module;
determining, by the control loop module, whether the audio signals received are affecting an individual's physiological state; and
upon determining that the audio signals received are negatively affecting the individual's physiological state, instructing one or more actuators to at least one of modify, decrease, cancel, drown out, or filter the audio signals received,
wherein the one or more actuators dynamically create or adjust the immersive environment based on at least one of (A) the physiological properties of the individual measured by the one or more physiological sensors or (B) properties of the surroundings of the individual measured by the one or more sensors, and pre-determined health and wellness goals set for the individual.

23. The computer implemented method of claim 22, wherein the one or more actuators dynamically create or adjust the immersive environment further based on an optimized set of control parameters used to drive the one or more actuators determined through a statistical analysis of measurements taken by the one or more audio sensors and wherein the optimized set of control parameters is based on historical data collected with respect to the properties of the individual's surroundings.

24. The computer implemented method of claim 23, wherein the statistical analysis of measurements taken by the one or more audio sensors include at least one of predictive modelling, machine learning, or data mining that analyze current and historical facts to make predictions about future or otherwise unknown events.

25. The computer implemented method of claim 23, wherein the optimized set of control parameters determined through the statistical analysis of measurements taken by the one or more audio sensors is based on the use of aggregated data to train a machine learning model to provide a custom user-specific experience, the aggregated data including properties measured from other individuals and retrieved from one of a cloud computing environment and one or more external devices.

* * * * *